United States Patent [19]
Reitter et al.

[11] Patent Number: 5,583,901
[45] Date of Patent: Dec. 10, 1996

[54] MEDICAL APPARATUS HAVING AN X-RAY DIAGNOSTICS INSTALLATION

[75] Inventors: Josef Reitter, Moehrendorf; Klaus Herrmann, Nuernberg, both of Germany

[73] Assignee: Siemens Aktiengesellschaft, Munich, Germany

[21] Appl. No.: 369,513

[22] Filed: Jan. 6, 1995

[30] Foreign Application Priority Data

Jan. 14, 1994 [DE] Germany ............... 44 00 997.6

[51] Int. Cl.[6] ................................... H05G 1/64
[52] U.S. Cl. ........................ 378/4; 378/65; 378/98.2
[58] Field of Search ................... 378/4, 146, 62, 378/63, 64, 98.8, 98, 98.2, 98.3, 98.11, 98.12

[56] References Cited

U.S. PATENT DOCUMENTS

| 5,117,445 | 3/1992 | Seppi et al. | 378/98.3 |
| 5,395,299 | 3/1995 | Herrmann et al. | 378/162 |

Primary Examiner—David P. Porta
Assistant Examiner—Don Wong
Attorney, Agent, or Firm—Hill, Steadman & Simpson

[57] ABSTRACT

A medical apparatus has an x-ray diagnostics installation which includes an x-ray source and a radiation reception arrangement having a radiation receiver that is mounted opposite the x-ray source and that can be rotated around an axis on a circular path synchronously with the x-ray source for imaging a discrete area lying on the axis. The x-ray source is activated during the rotating and the radiation reception arrangement integrates signals corresponding to the received radiation.

22 Claims, 7 Drawing Sheets

MEDICAL APPARATUS HAVING AN X-RAY DIAGNOSTICS INSTALLATION

BACKGROUND OF THE INVENTION

1. Field of the Invention

The present invention is directed to a medical apparatus having an x-ray diagnostics installation which includes an x-ray source and a radiation reception means having a radiation receiver that is mounted lying opposite the x-ray source.

2. Description of the Prior Art

Apparatuses of the above general type are known in the art. When the x-ray source and the radiation receiver are stationary given transirradiation of a subject to be examined and located between the x-ray source and the radiation receiver, an x-ray shadowgraph that offers a good overview of the anatomical conditions of the subject in many instances arises.

In instances wherein a diagnostically relevant area cannot be imaged with adequate clarity in an x-ray shadowgraph, there is the possibility of preparing what is referred to as an x-ray tomogram on the basis of an appropriately controlled motion of the x-ray source, radiation receiver and subject under examination, whereby only the slice of the subject under examination which contains the respective, diagnostically relevant area is sharply imaged as a consequence of blurring phenomena outside that area. The technological outlay that must be exerted in order to equip an apparatus of the type initially cited such that it is possible to produce x-ray tomograms is relatively high and is reflected in corresponding costs. Such an option is therefore frequently foregone, even though it would basically be desirable to have a possibility available for preparing x-ray tomograms, particularly for displaying discrete, diagnostically relevant regions, for example tumors or body calculi (for example, kidney stones or gall stones).

German OS 35 26 850 discloses another apparatus that enables the preparation of tomograms. In this apparatus, only the x-ray source and the radiation receiver are moved for producing the tomogram. The radiation receiver is an x-ray image intensifier having a following video chain. The x-ray source and the x-ray image intensifier are pivoted in common around a swiveling axis, and the swivel angle is monitored with an angle transmitter. X-ray images are produced and stored at defined angular positions. The stored x-ray images are computationally projected into a plane within an image processor, taking the respective swivel angle into consideration, and are superimposed to form a corresponding tomogram. It is thus clear that high technological outlay must also be made in conjunction with the production of tomograms.

SUMMARY OF THE INVENTION

It is an object of the present invention to provide an apparatus of the type initially cited with which discrete areas can be imaged without being covered by other anatomical structures in the resulting x-ray image.

This object is inventively achieved in a medical apparatus having an x-ray diagnostics installation that includes an x-ray source and a radiation reception means having a radiation receiver that is mounted opposite the x-ray source and that can be rotated around the axis on a circular path synchronously with the x-ray source for imaging a discrete, diagnostically relevant area lying on an axis, with the x-ray source being activated during the rotating and the radiation reception means integrating the received radiation. Only subjects lying directly on the axis are thus sharply imaged. Subjects lying at a greater distance are imaged blurred and are increasingly unsharp the farther they lie from the axis. Given relatively small swiveling angles, for example 5°, subjects that are at a distance of a few centimeters from the axis are imaged sharply enough so that diagnostically interpretable image information is still present. The distance from the axis up to which a sharpness that is still adequate for diagnostic purposes is present becomes smaller as the swiveling angle increases. It is thus clear that the invention makes it possible to image a discrete, diagnostically relevant area lying on the axis even when this area is actually covered with other anatomical structures. For this purpose, there must merely be the possibility of being able to swivel the x-ray source and the radiation receiver synchronously on a respective circular path around the axis, this already being the case in many medical apparatus as having an x-ray diagnostics installation, and there must also be the possibility of being able to integrate the x-radiation received with the radiation receiver during the swiveling. No special outlay need be made for this purpose either since, for example, given an x-ray film or of a storage phosphor employed as a radiation receiver, the integration of the received x-radiation is an inherent property of the radiation receiver.

According to a preferred embodiment of the invention, the radiation reception means comprises an x-ray image intensifier video chain. In this, embodiment as well, the outlay for effecting the integration of the radiation received during swiveling is extremely slight. Care must be exercised to insure, that the scanning of the target of the video camera only ensues at the end of the swivel event. When the output signals of the x-ray image intensifier video chain are subjected to an analog-to-digital conversion, there is the possibility of supplying the corresponding digital signals to an integrating digital memory that accomplishes the required integration during the swivel event. No special outlay is required here either since digital x-ray image intensifier video chains usually already have integrating memories available to them that usually operate according to the principle of moving weighted averaging (MWA).

In a preferred version, the swiveling ensues in the form of a pendulum motion around a middle position.

A medical apparatus constructed in accordance with the principles of the present invention may also include a radiation source for treatment of a body area, for example a tumor or a body calculus, that can be located with the x-ray diagnostics installation, such that the body area can be exactly located even under unfavorable anatomical conditions, for example when covered by bone structures or intestinal gas, as is the case, for example, in lithotripsy given ureter stones lying in the pelvic region. Since it is essentially only subjects lying on the axis that are sharply imaged in the images of the inventive x-ray diagnostics installation, it is also easily possible under unfavorable conditions to position the body area to be treated, for example a tumor or a calculus, in the required way on the basis of the images of the x-ray diagnostics installation such that the body area assumes the position required for treatment with the radiation source, this position preferably lying on the axis. The locating of the body area to be treated thereby ensues in a known way by transirradiation with the x-ray diagnostics installation from different directions, whereby a common swivelling of the x-ray source and takes place while the x-ray source is the radiation receiver activated and integration of the received radiation ensues for at least one transirradiation direction in the way set forth above.

Operation of the apparatus becomes especially simple and time-saving when, for transirradiation from different directions, the x-ray diagnostics installation is adjustable into transirradiation positions corresponding to the different directions by synchronously swiveling the x-ray source and the radiation receiver around the axis, and the x-ray source is activated shortly before reaching a transirradiation position and the integration is begun. An apparatus motion that is required anyway is then utilized for imaging. Alternatively, the synchronous swiveling can ensue around a transirradiation position which is a middle position. This is especially expedient when the radiation source has an x-ray-transparent area through which the x-radiation emanating from the x-ray source passes in the transirradiation direction forming the middle position.

The apparatus of the invention can be used for monitoring the disintegration of a stone in the case of an apparatus provided for lithotripsy. According thereto, the image produced by synchronous swiveling with integration is employed, so to speak, as a "blank image" and is subtracted from a "life image" having a corresponding projection. A clearer presentation of the larger fragments of a partially disintegrated stone is achieved as a result whereas small fragments, referred to as stone rubbish and grits, are not presented or respectively, are presented substantially more weakly. A more uniform overall image impression derives, so that less blooming occurs at the monitor and less irradiation of the eye of the attending physician upon observation of the image occurs given a windowing with limitation to the relevant image parts. The vignetting of the x-ray image intensifier video chain, that is particularly disturbing given windowing, is also eliminated.

The subtractor also provides the possibility of subtracting an image having a first integration time that is generated given a stationary x-ray diagnostics installation, from an image generated with a shorter integration time with at least essentially the same transirradiation direction and with the x-ray diagnostics installation being likewise stationary. Diagnostically relevant areas, or body areas to be treated, that move as a consequence of the respiration of the examination subject are thereby clearly imaged. Since, bone structures do not move or move only minimally as a consequence of the respiration of the examination subject, the image having the longer integration time represents, so to speak, a "blank image" wherein the diagnostically relevant subject that moves as a consequence of the respiration is imaged unsharp. When this "blank image" is subtracted from a "life image" having a shorter integration time, the bone structures disappear and the diagnostically relevant subject or the body area to be treated becomes highly visible. After windowing the image, that zone within which the diagnostically relevant subject or the body area to be treated moves also usually becomes clearly visible. A more uniform image impression is also achieved, so that irradiation of the image intensifier and of the eye are also avoided. Moreover, the vignetting of the x-ray image intensifier video chain is again also eliminated. It is clear that the subtraction of two images having respectively different integration times can also ensue given a medical apparatus whose x-ray diagnostics installation does not offer the possibility of synchronous swiveling with integration of the received radiation.

An enhancement of contrast is achieved by using a method disclosed by German OS 35 26 903 in that the radiation receiver is irradiated with a constant dose following the actual exposure, the image contribution made by this constant dose being in turn eliminated during the further course of the image processing steps. It is evident that a clearer imaging of moving areas is not possible using this known method by itself.

The radiation source can be activated by control pulses to emit radiation pulses, the control pulses being synchronized with the x-ray image intensifier video chain such that the emission of a radiation pulse ensues substantially simultaneously with the appearance of the vertical pulse of the video camera of the x-ray image intensifier video chain. As a result thereof, it is possible to check, for example with a graticule mixed into the x-ray image, whether the body area to be treated is in fact located at the location—marked by the graticule—required for a successful implementation of the treatment at the point in time the radiation pulse is triggered.

According to an embodiment of the invention, a source of focused acoustic waves is provided as the radiation source. The focus zone of the focused acoustic waves thereby expediently lies on the axis, at least during the treatment, thereby facilitating the positioning of a body area to be treated into the focus zone.

When the medical apparatus is provided for lithotripsy, the radiation source is a shockwave source with which shockwaves whose intensity is adequate for the disintegration of body calculi can be generated.

DESCRIPTION OF THE DRAWINGS

An exemplary embodiment of the invention is described in the attached drawings with reference to a lithotripsy apparatus.

DESCRIPTION OF THE PREFERRED EMBODIMENTS

Figure 1:
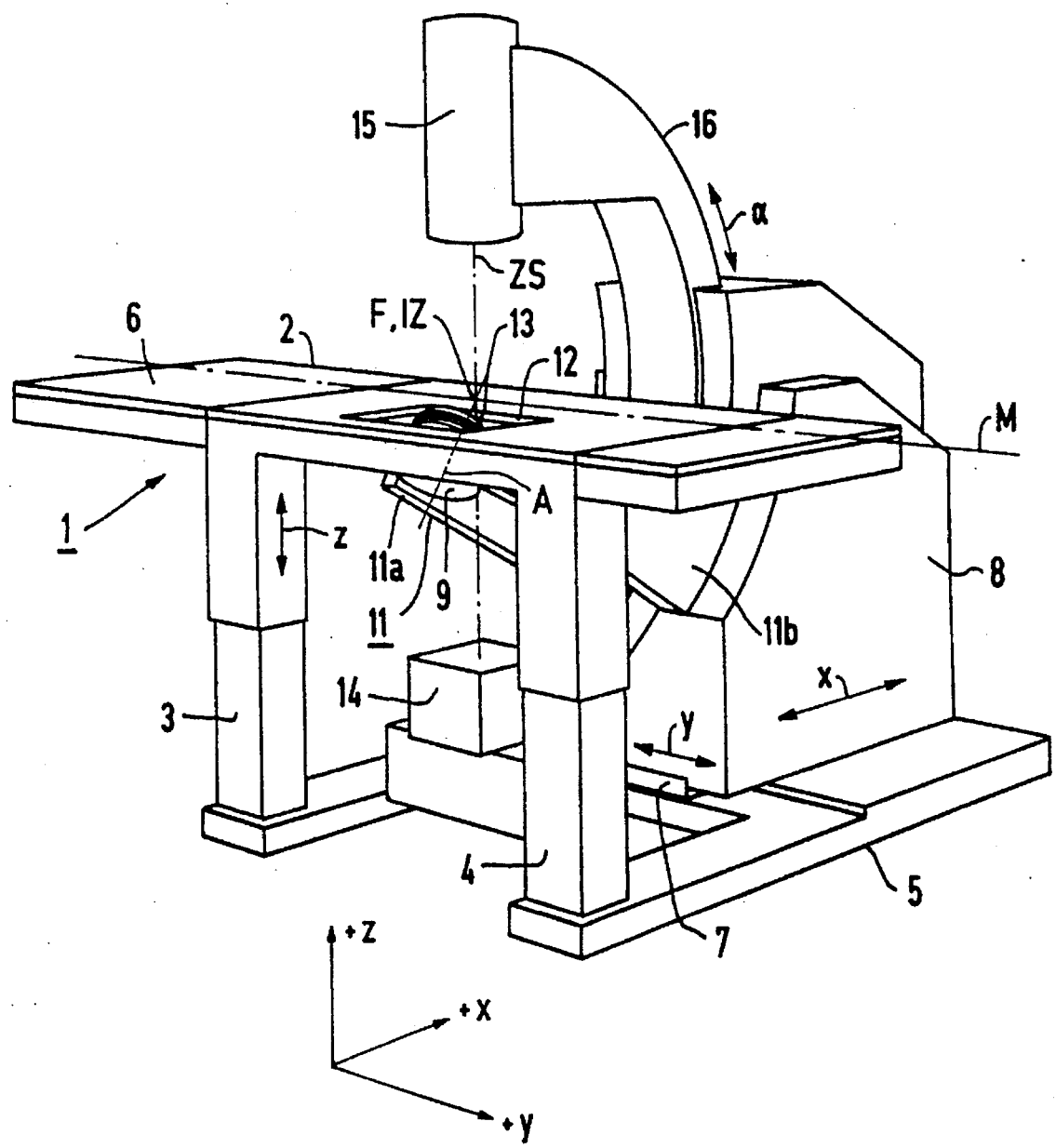
FIG. 1 shows a lithotripsy apparatus constructed in accordance with the principles of the present invention shown in a perspective illustration.

As shown in FIG. 1, the medical apparatus of the invention has a support table generally referenced 1 for a subject to be treated, the support plate 2 thereof being height-adjustable with reference to a pedestal 5 by means of two telescoping columns 3 and 4. The support plate 2 is height-adjustable in a known way (not shown) in the direction of the double arrow z, and thus parallel to the z-axis of the spatial (Cartesian) coordinate system shown in FIG. 1.

A carriage 7 is seated on the pedestal 5 adjustable in a straight-line fashion in the direction of the longitudinal axis of the support plate 2, which proceeds parallel to the x-axis of the spatial coordinate system. The displacement of the carriage 7 is indicated by a double arrow y. A support part generally referenced 8 is seated on the carriage 7 so as to be longitudinally displaceable in a direction proceeding transversely relative to the longitudinal axis of the support plate 2, and thus parallel to the x-axis of the spatial coordinate system. This is indicated by the double arrow x.

The adjustment of the support part 8, of the carriage 7 and of the support plate 2 in the respective directions of the double arrows x, y, z ensues in a way not shown in detail with suitable motors, particularly electric motors, and suitable, particularly mechanical, gearings as required.

The medical system also has a source 9 of focused acoustic waves, this source 9 being, for example, an electromagnetic pressure pulse source of the type disclosed in European Application 0 372 119, corresponding to U.S. Pat. No. 4,984,565. The source 9 has an acoustic axis A on which the focus zone F of the acoustic pressure pulses generated by the source 9 lies. U.S. Pat. No. 4,647,505 and European Application 0 188 750, corresponding to U.S. Pat. No. 4,697,588, are also referenced for further details regarding electromagnetic pressure pulse sources, the disclosure of these references being incorporated herein by reference.

The source 9 is attached to a source carrier 11 having two arms 11a and 11b, which is in turn attached to the support part 8 so as to be longitudinally displaceable such, so the source 9 can be adjusted on a straight line from a standby position into the working position shown in FIG. 1 in the direction of the double arrow w. When the source 9 assumes its working position, the focus F is located in an isocenter IZ above the support surface 6 of the support plate 2. The acoustic axis A of the source 9 then extends through the isocenter IZ. In its working position, the source 9, moreover, projects through an opening 12 of the support plate 2 with a flexible bellows-like application cushion 13 that serves the purpose of application to a subject to be treated. In its standby position, the source 9 is retracted in the direction of the double arrow w to such an extent in the direction toward the support part 8 that the application cushion 13 does not project through the opening 12 of the support plate 2.

An x-ray diagnostics installation is also attached to the support part 8, this x-ray diagnostics installation including, among other things, an x-ray radiator 14 as an x-ray source and an x-ray image intensifier 15 lying thereto as a radiation receiver. The x-ray image intensifier 15 is a component of an x-ray image intensifier video chain forming a radiation reception means. The x-ray radiator 14 and the x-ray image intensifier 15 are attached to the ends of an arcuately curved C-arm 16. The C-arm 16 is attached to the support part 8 so as to be adjustable along its circumference in the direction of the curved double arrow α. Stated more precisely, the C-arm 16 can be rotated around its middle axis M. The central ray ZS of the x-ray beam of the x-ray diagnostics installation (i.e., from the x-ray radiator 14) intersects the middle axis M of the C-arm 16 at a right angle. The C-arm 16 is also attached to the support part 8 such that the middle axis M of the C-arm 16 and the central ray ZS proceed through the isocenter IZ. The central ray ZS of the x-ray diagnostics installation thus proceeds through the isocenter IZ for any desired swiveled position of the C-arm 16.

Both the adjustment of the source 9 from its standby position into its working position and vice versa in the direction of the double arrow w, and the rotation of the C-arm 16 in the direction of the double arrow α ensue under motor drive in a way that is not shown, preferably electromotively and with suitable gearings as necessary.

Figure 3:
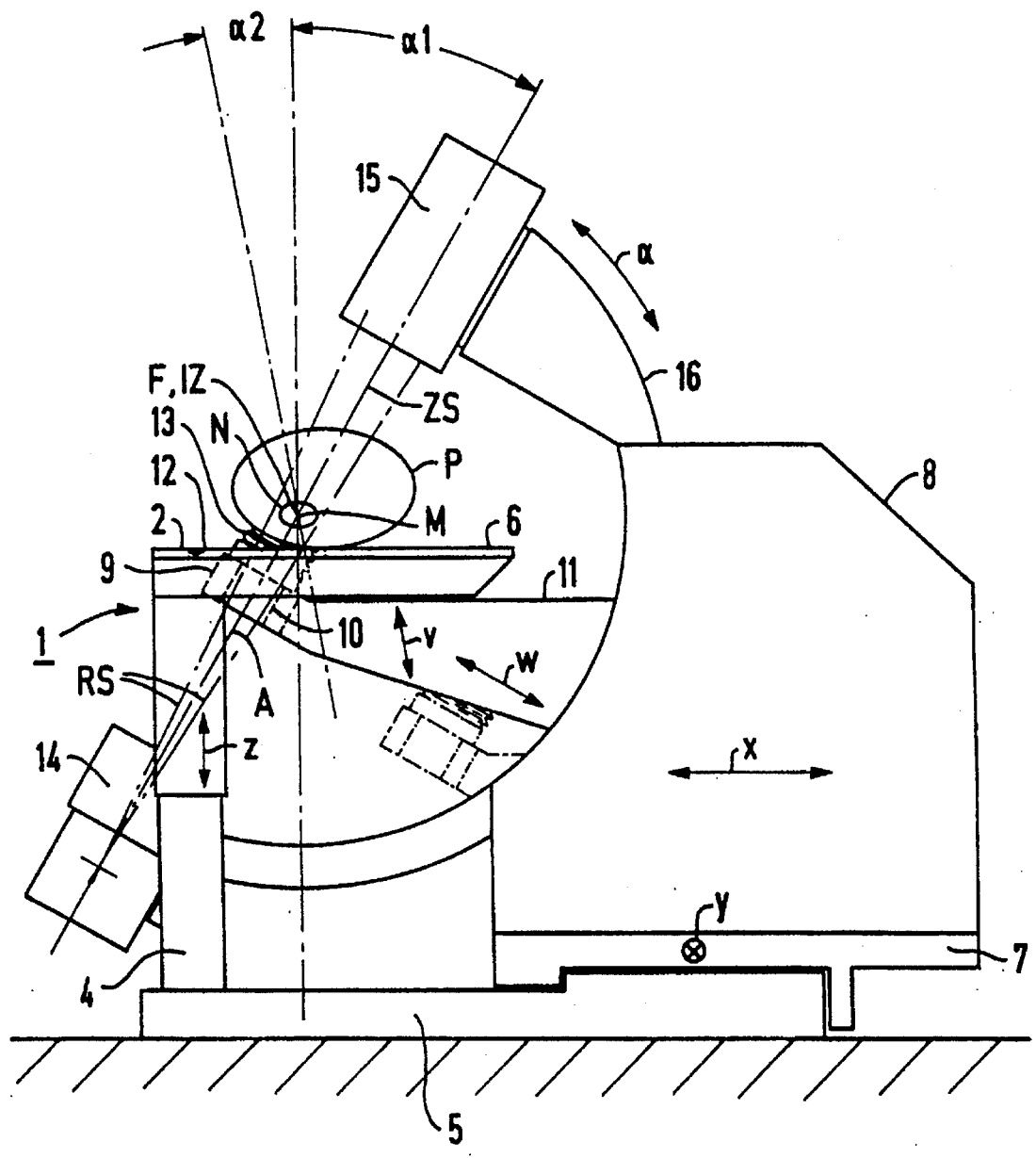
FIGS. 3–7 respectively show different operating conditions of the lithotripsy apparatus of FIGS. 1 and 2.
Figure 4:
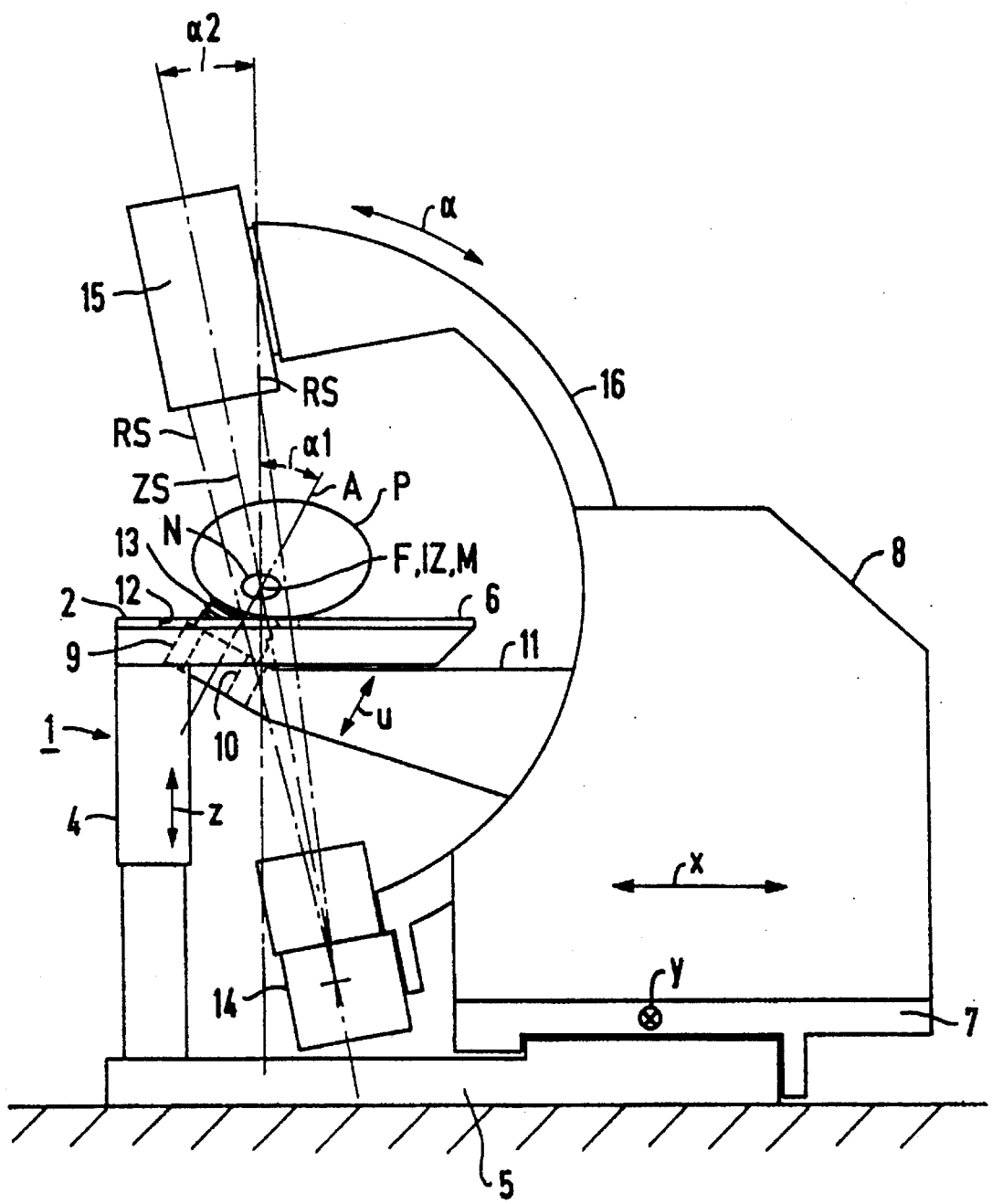

In order to spatially locate a body area to be treated, for example a kidney stone, in a subject to be treated, for example a patient, with the x-ray diagnostics installation—in this respect, the body area to be treated is also a diagnostically relevant area and in order to be able to adjust this body area to be treated into the isocenter IZ and thus into the focus zone F of the source 9 in its working position, the patient is transirradiated from two different directions with the x-ray diagnostics installation in a known way in order to obtain the required information about the spatial position of the kidney stone. For setting the first transirradiation direction, the C-arm 16 is rotated with reference to the viewing direction of FIG. 1—in a clockwise direction by an angle α1 of 30° proceeding from its position shown in FIG. 1 wherein the central ray ZS proceeds vertically. In this position, which is shown in FIG. 3, the central ray ZS and the acoustic axis A of the source 9 in its working position coincide. Consequently, the useful x-ray beam proceeds through an x-ray-transparent area 21 of the source 9 when the latter assumes its working position. In the second transirradiation direction, shown in FIG. 4, the C-arm 16 is rotated counterclockwise by a few degrees, for example an angle α2 of 10°, relative to the position shown in FIG. 1. The useful x-ray beam essentially passes by the source 9 in its working position in this orientation, so that no significant degradation of the image information available in the second transirradiation direction occurs.

Figure 2:
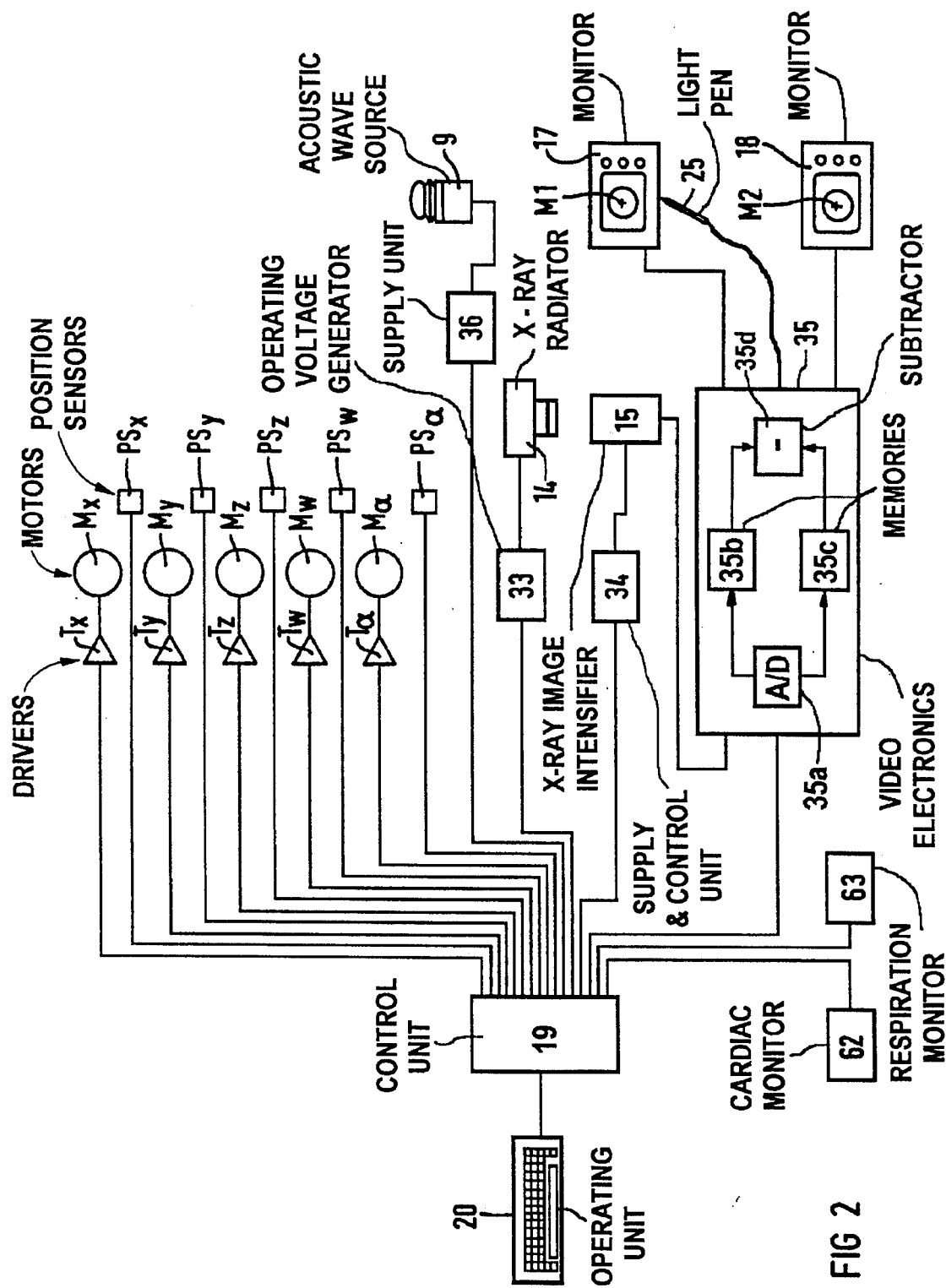
FIG. 2 is a schematic illustration of a part of a block circuit diagram of the lithotripsy apparatus of FIG. 1.

As shown in FIG. 2, monitors 17 and 18 are respectively provided for each of the two transirradiation directions for displaying the corresponding fluoroscopic images, that can also be stored in an image memory. Cruciate marks M1 and M2, which indicate the position of that point wherein the central ray ZS intercedes the image plane of the image are respectively mixed into the image of each of the monitors 17 and 18. When the image of a specific body area coincides with the respective mark M1 or M2 in both images, this means that the body area is located in the isocenter IZ.

A control unit 19 to which an operating unit 20, for example in the form of a keyboard, is connected in addition to other operating facilities not shown in FIG. 2 is provided for the control and operation of the medical system.

The motors $M_x$, $M_y$, $M_z$, $M_w$ and $M_\alpha$ that effect the above-described adjustment motions in x, y, z, w and α direction are connected to the control unit 19 via driver stages $T_x$, $T_y$, $T_z$, $T_w$ and $T_\alpha$.

Position sensors $PS_x$, $PS_y$, $PS_z$, $PS_w$ and $PS_\alpha$ are also connected to the control unit 19, which respectively supply signals corresponding to the position of the support part 8 relative to the carriage 7, the carriage 7 relative to the pedestal 5, the support plate 2 relative to the pedestal 5, the source 9 relative to the support part 8 and of the C-arm 16 relative to the support part 8.

An operating voltage generator 33 that supplies the x-radiator 14 with the voltages and currents required for the operation thereof, a supply and control unit 34 for the x-ray image intensifier 15 belonging to the x-ray image intensifier video chain, and video electronics 35 allocated to the x-ray image intensifier 15, to which the output signals of the video camera belonging to the x-ray image intensifier 15 are supplied, are also connected to the control unit 19.

The monitors 17 and 18 are connected to the video electronics 35. Among other things, the video electronics 35 effects the mixing of the marks M1 and M2 into the images of the monitors 17 and 18.

A cardiac monitor 62 for the acquisition of heart activity (ECG) signals and a respiration monitor 63 for the acquisition signals indicative of the respiratory activity of the patient are additionally connected to the control unit 19. The monitors 62 and 63 each include suitable sensors (not shown), i.e. at least one ECG electrode, or a respiration belt or the like, and the electronics required for processing the signals supplied by the respective sensor.

The signals or data representing the cardiac and respiratory activity are supplied to the control unit 19, which uses the data in the manner disclosed in German OS 36 21 935 to emit shockwaves only when the movement of the calculus to be disintegrated is minimum as a consequence of the respiratory activity of the patient, and when there is no risk of triggering disturbances in the heart rhythm in the case of the patients having unstable heart activity. To this end, the control unit 19 compares the signals or data representing the respiratory activity to a threshold and only enables shockwaves to be emitted when the threshold is not upwardly exceeded, i.e. when the patient has at least largely exhaled. The control unit 19 evaluates the data representing the heart activity so that it detects the R-wave of the ECG. When the heart activity of the patient is taken into consideration in addition to the respiratory activity, shockwaves can only be triggered when the threshold is downwardly exceeded and when an R-wave also occurs, or when a defined time span following the appearance of the last R-wave has elapsed.

Finally, the supply unit 36 for the source 9 is connected to the control unit 19.

The functioning and the operation of the system according to FIGS. 1 and 2 shall be set forth in greater detail below.

When the system is placed in operation, the mechanical components of the system are automatically brought into a basic position, insofar as this is not already the case. Corresponding data are stored in the control unit 19. In the basic position, the source 9 assumes its standby position. The support plate 2 is moved into its lowest position. The support part 8 assumes its position farthest from the support table 1. The carriage 7 assumes a medium position on the pedestal 5. The attainment of the basic position is recognized by the output signals of the corresponding position sensors. The basic position, moreover, can also be produced during operation by activating a corresponding key of the operating unit 20.

In response to the actuation of a key of the operating unit 20, the control unit 19 drives the system as directed by the actuated key, taking the signals of the position sensors into consideration as necessary. This situation need not be set forth in further detail below; it shall only be mentioned that a specific operation is carried out in response to the actuation of a corresponding key.

A patient to be treated can be placed on the support plate 2 in the basic position such that the body region to be treated is located above the opening 12. The locating and positioning event, which serves the purpose of bringing the body region to be treated, for example a kidney stone, into the isocenter IZ, and thus into the focus zone F of the source 9 in its working position, is initiated by actuating a corresponding key of the operating unit 20.

Thereafter, first the carriage 7, then the support part 8 are adjusted such that the isocenter IZ is located centrally over the opening 12. The support plate 2 is then adjusted upward to such an extent that the isocenter IZ is located approximately 100 mm above the support plate 2. Moreover, the C-arm 16 is rotated in the direction toward its position corresponding to the first transirradiation direction, but is stopped shortly before it reaches this position, i.e. at an angle of, for example, 5°–10° that can be set with the operating unit 20 corresponding to the respective requirements.

The control unit 19 then sets the tube voltage and the tube current of the x-radiator 14 to values preselected with the operating unit 20 corresponding to the respective requirements.

The transirradiation ensues only when a corresponding key of the operating unit 20 is actuated, such that the control unit 19 now rotates the C-arm 16 into its position corresponding to the first transirradiation direction and thereby activates the x-radiator 14 and the x-ray image intensifier 15 for the duration of the rotating motion via the operating voltage generator 33 and the supply and control unit 34 of the x-ray image intensifier 15. The output signals of the video camera of the x-ray image intensifier video chain corresponding to the received radiation are supplied—after passing through an analog-to-digital converter 35a contained in the video electronics 35—to a digital image memory 35b of the video electronics 35 allocated to the first transirradiation direction, wherein the signals are digitally integrated, preferably in a known way according to the principle of sliding weighted averaging. The video electronics continuously displays the corresponding image on the monitor 17 together with the mark M1.

The manner by which the carriage 7 must be adjusted in the y-direction and the manner by which the support part 8 must be adjusted in the x-direction in order to bring the body area to be treated into the coincidence with the mark M1 can now be seen on the basis of the x-ray image displayed on the monitor 17, only the body regions lying in the region of the middle axis being sharply shown therein as a consequence of blur phenomena. The adjustment of the carriage 7 and the support part 8 preferably ensues automatically, by marking the image of the body area to be treated in the corresponding image in the first transirradiation direction with a light pen 25 connected to the video electronics 35, whereupon the video electronics 35 emits appropriate signals to the control unit 19 that initiate the required adjustment motions.

When the adjustment procedure that is required in order to bring the body area to be treated into coincidence with the mark M1 has been ended, the second transirradiation direction is set by actuating a corresponding key of the operating unit 20.

Analogously to the fashion set forth in conjunction with the first transirradiation direction, transirradiation of the second direction also ensues proceeding from a position of the C-arm 16 that lies shortly before the position of the C-arm corresponding to the second direction is reached, i.e. by an angle of, for example, 5°–10° that can be set with the operating unit 20 in conformity with the respective requirements and that is preferably of the same size as in the case of the first transirradiation direction.

The output signals of the video camera of the x-ray image intensifier video chain arising during a subsequent rotation of the C-arm 16 into the position corresponding to the second transirradiation direction are processed in a way analogously to the first direction, the video electronics 35 having an image memory 35c corresponding to the second transirradiation direction wherein the signals are digitally integrated. The video electronics 35 continuously displays the image corresponding to the second transirradiation direction on the monitor 18 together with the mixed-in mark M2. The control unit 19 appropriately switches the output of the A/D converter 35a to direct the output signals thereof to the appropriate memory 35b or 35c.

Since the body area to be treated is already located on the central ray belonging to the first transirradiation direction, the body area to be treated can now be brought into coincidence with the mark M2, and thus into the isocenter IZ, on the basis of a relative motion of the body area to be treated and the isocenter IZ in the direction of the central ray belonging to the first transirradiation direction.

This again occurs by marking the image of the body area to be treated is marked with the light pen 25 in the image corresponding to the second transirradiation direction, whereupon the control unit 19 initiates the required adjustment motion.

When the body area to be treated is in coincidence with the mark M1 on the image of the monitor 17 and is also in coincidence with the mark M2 in the image of the monitor 18, the source 9 can be brought from its standby position into its working position by actuating a corresponding key of the operating unit 20, the source 9 pressing against the body surface of the patient with the application cushion 13 in this working position, i.e. being applied. If there is the risk that the body area to be treated will thereby be moved out of the isocenter IZ, a fine locating event expediently follows.

Using the stored data relating to of the second transirradiation direction, the x-ray diagnostics installation is activated for fine locating via a corresponding key of the operating unit 20. Upon activation of the x-ray image intensifier video chain and the x-radiator 14, the C-arm 16 is thereby rotated around its position corresponding to the second transirradiation direction as a middle position in a pendulum motion by an angle αS of, for example, ±5° that can preferably be set with the operating unit 20 and by integration of the output signals of the video camera of the x-ray image intensifier video chain. The video electronics 35 continuously displays the image obtained in this way on the monitor 18. As used herein a pendulum motion is a motion along a circular circumference proceeding from the middle position through the angle αS in one direction, and from therethrough twice the angle αS in the other direction, and from this position back through the angle αS into the middle position.

If a dislocation of the image of the body area to be treated relative to the mark M2 has occurred, this can be corrected in the above-described way by marking the image of the body area to be treated with the light pen 25.

When the image of the body area to be treated and the mark M2 continue to be in coincidence, or are again in coincidence, a switch into the first transirradiation direction is made by actuation of a corresponding key of the operating unit 20. When this first transirradiation direction has been reached, an updated x-ray image is produced by actuation of a corresponding key of the operating unit 20 in the above-described way by pendulum motion around the position of the C-arm 16 corresponding to the first transirradiation direction with integration of the output signals of the video camera of the x-ray image intensifier video chain. This updated x-ray image is continuously displayed on the monitor 17 by the video electronics 35.

Figure 5:
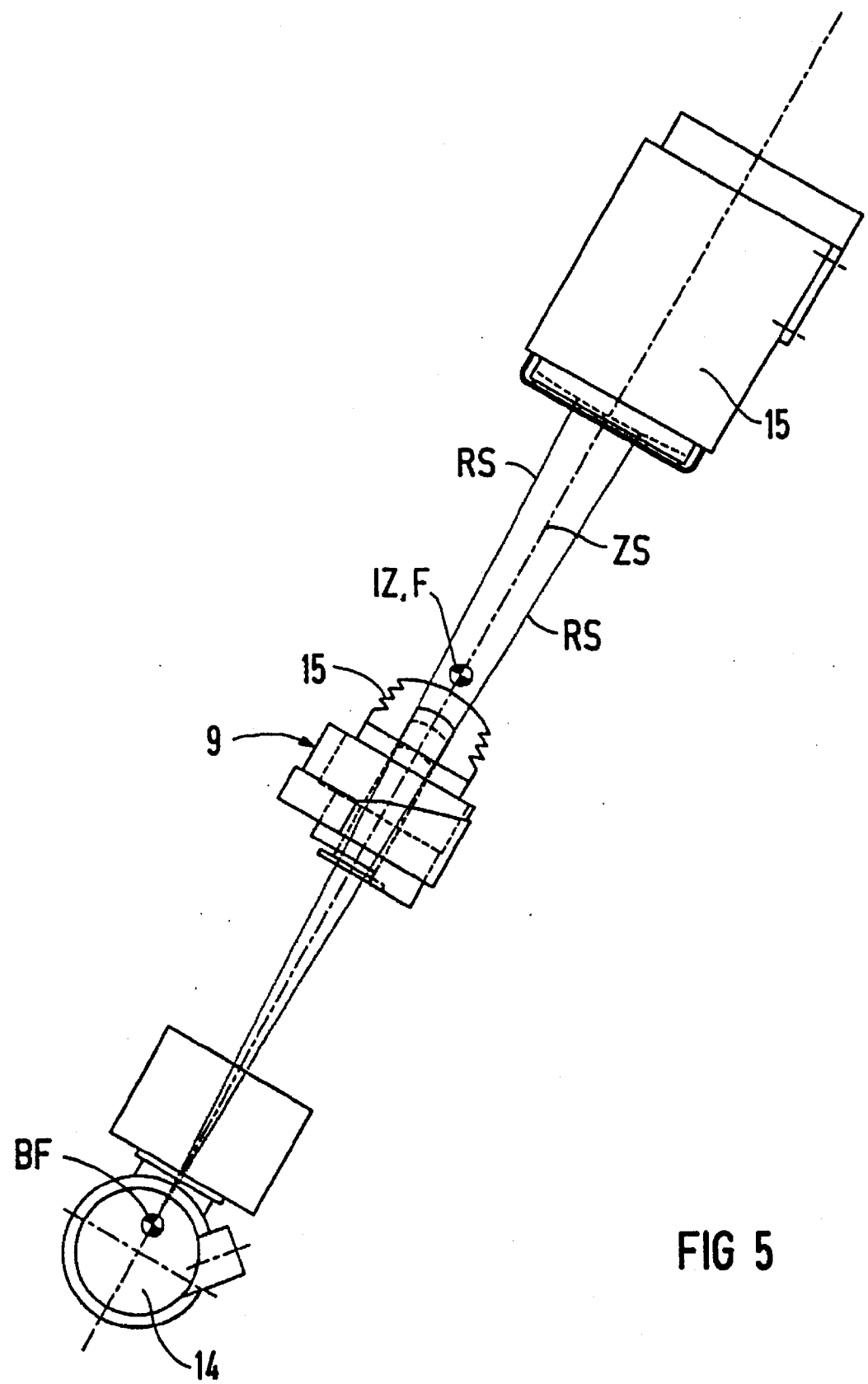
Figure 6:
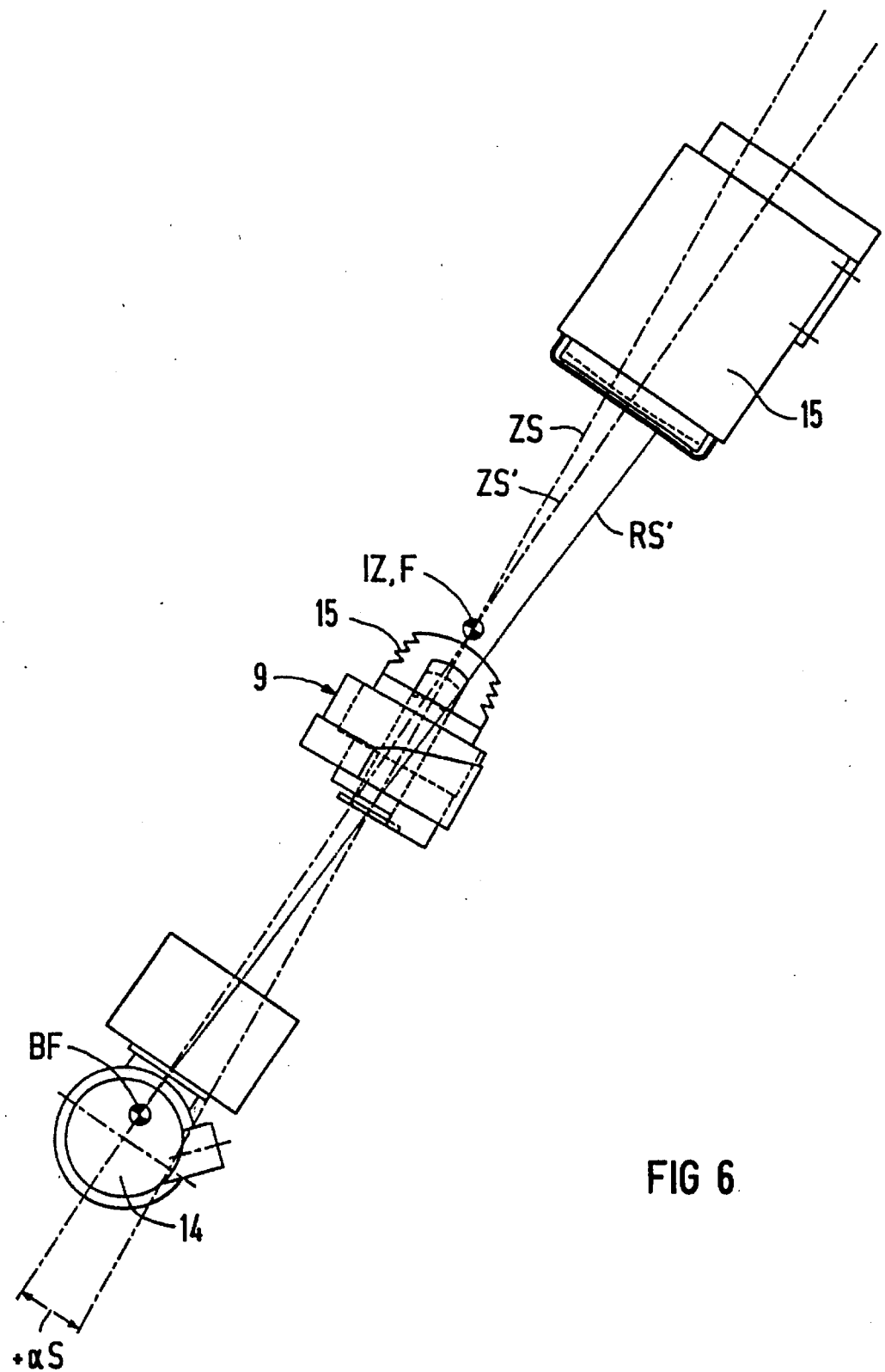
Figure 7:
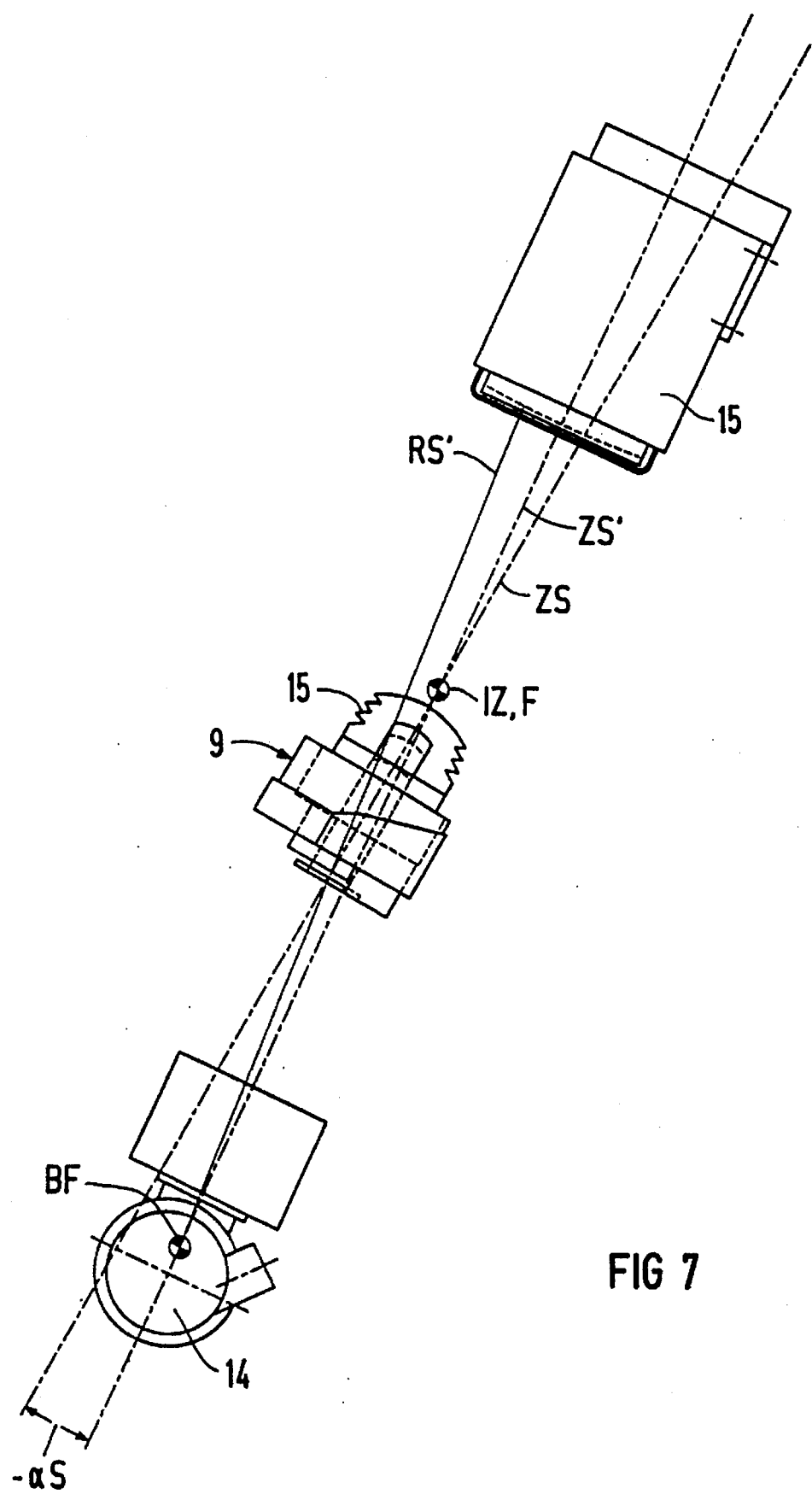

Since the central ray of the x-ray diagnostics installation proceeds through the x-ray-transparent region 21 of the source 9 in the first transirradiation direction during the fine locating event, the possible range of rotation of the C-arm 16 is limited by the dimensions of the x-ray-transparent region 21. This is illustrated in FIGS. 5–7. FIG. 5 shows the first transirradiation direction as middle position of the pendulum motion. FIG. 6 shows the maximally possible amplitude of the pendulum motion in the direction in a clockwise direction. FIG. 7 shows the maximally possible amplitude of the pendulum motion in the counterclockwise direction. The position of the central ray for the second transirradiation direction is referenced ZS in FIGS. 5–7. ZS' indicates the position of the central ray for the illustrated maximum amplitude, this also showing the one marginal ray of the x-ray beam that emanates from the focal spot (referenced BF) of the x-ray 14 that passes through the x-ray transparent region 21 of the source 9. The other marginal ray is referenced RS'. The marginal rays of the x-ray beam passing through the x-ray-transparent region 21 of the source in the case of FIG. 5 are referenced RS.

Possible dislocations of the body area to be treated relative to the mark M1 can now be eliminated by a relative motion of the body area to be treated and the isocenter IZ in the direction of the central ray for the second transirradiation direction, since the body area to be treated is already located on the central ray of the second transirradiation direction. The corresponding relative motion is effected in the above-described way by marking the image of the body area to be treated with the light pen 25.

When, after the end of the fine-locating event, (if needed) the marks M1 and M2 are in coincidence with the image of the body area to be treated in the respective images of the monitors 17 and 18, the treatment with focused acoustic waves can begin. Using corresponding keys of the operating unit 20, one can select the pressure of the shockwaves in conformity with the respective treatment case. One can also select the number of shockwaves to correspond to the respective treatment case using appropriate keys of the operating unit 20. When the pressure of the shockwaves and the number of shockwaves have been selected, the emission of shockwaves can be started by actuation of a corresponding key of the operating unit 20. The emission of shockwaves can be stopped at any time by actuating another key of the operating unit 20.

In order to be able to monitor the treatment procedure, there is the possibility at any time of causing the production of an updated image by actuating a corresponding key of the operating unit 20, this updated image being stored in the video electronics 35 and being continuously displayed on the monitor 17. The production of the updated x-ray image ensues in the form of a conventional fluoroscopic image given a stationary x-ray diagnostics installation.

In order to make it possible to check whether the body area to be treated is really located in the isocenter during the output of shockwaves, an operating mode can be set by a corresponding actuation of the operating units 20 wherein the emission of shockwaves ensues not only dependent on the respiratory activity and/or on the heart activity of the patient in the way already set forth, but also ensues dependent on the vertical pulses of the video camera belonging to the x-ray image intensifier video chain that respectively appear at the beginning of the generation of a new frame or field. The control unit 19 only triggers a shockwave when this is possible on the basis of the monitored physiological function or functions of the patient and when a vertical pulse of the video camera also appears. The emission of shockwaves is synchronized with the image generation of the x-ray image intensifier video chain in this way such that the image displayed on the monitor 17 substantially represents the point in time of the emission of the shockwave. A check can thus be made to determine whether the body area to be treated is correctly positioned during shockwave emission. It is expedient for a good image quality to employ an increased dose rate at the input luminescent screen of the x-ray image intensifier 15 in the described operating mode. Since the triggering of shockwaves usually ensues with a frequency on the order of magnitude of approximately 1 Hz, an overload of the x-ray tube need not be feared. The load of the x-ray tube can be lowered further because of the extremely short pulse direction of approximately 2–100 ms (preferably, 45 ms) when the production on updated x-ray image in the described operating mode ensues only at every second or third shockwave.

When an updated x-ray image indicates that a realignment of the body area to be treated is required, this is possible without further difficulty by undertaking a repeated locating event, which may possibly be limited to the fine locating event.

In another operating mode that can be set with the operating unit 20, the production of updated images ensues using a subtractor 35d that is contained in the video electronics 35. This occurs in such a way that an image having a long integration time, i.e. an integration time corresponding in terms of order of magnitude to the reciprocal of the respiratory rate of the patient, is first stored in one of the memories 35b or 35c given a stationary x-ray diagnostics installation, and it is then subtracted from a current image or "life image" with the subtractor, this "life image" being registered with a short integration time, i.e. with an integration time that is adequate in order to avoid image noise. Dependent on the respiration rate of the respective patient, the longer integration time consequently lies on the order of magnitude of approximately 320–1280 ms and the shorter integration time lies in the range from 80–320 ms, whereby the longer integration time should always be at least four times as long as the shorter integration time.

If the body area to be treated moves as a consequence of respiratory activity but disturbing anatomical structures, for example bone structures, adjacent thereto in the x-ray image remain essentially immobile, the structures at rest disappear in the image obtained by subtraction. Only the body area to be treated is displayed sharply, at that location at which it was located upon production of the image having the shorter integration time. The body area to be treated does not appear in the subtraction image since the body area to be treated is only presented blurred in the image having the long integration time. The zone within which the body area to be treated moves as a consequence of the respiratory activity can be made clearly visible by windowing the substraction image. As a result, important, additional information is available to the attending physician.

The subtractor 35c contained in the video electronics 35 can also be used when the image generated during the locating of the body area to be treated ensues with rotation of the C-arm 16 and integration of the received radiation. A normal fluoroscopic image that is made with the C-arm 16 in a position corresponding to the respective transirradiation direction and with an integration time of 80–320 ms. This image is subtracted from an image produced in the same way, but the integration time thereof preferably lying on the order of magnitude of 320–5000 ms. Apart from the fact that subtraction images produced in this way are also well-suited for locating purposes due to the disappearance of bone structures, that are still visible in the image registered with a stationary x-ray diagnostics installation, it is possible in the case of lithotripsy to use such images to check the extent to which the disintegration of a calculus to be disintegrated has progressed. A clearer illustration of the larger fragments of a partially disintegrated stone arises in such a subtraction image, whereas smaller fragments, referred to as stone rubbish and grits, are not displayed or are displayed more weakly. The informational content of the subtraction image can also be further enhanced by windowing.

The book "Imaging Systems für Medical Diagnostics", edited by Erich Krestel, 1990, Siemens AG, particularly pp. 331–369, whose content is incorporated herein by reference describes the functioning of the memory contained in the video electronics 35 that effects the integration by moving weighted sliding averaging, as well as the windowing of x-ray images.

The invention has been set forth above with reference to the example of a lithotripsy apparatus, however, it can also be utilized in other medical systems as desired. The invention can be used in diagnostic and/or therapy apparatuses.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical apparatus comprising:

an x-ray diagnostics system having an x-ray source and a radiation receiver which produces electrical signals corresponding to x-rays incident thereon;

an x-ray image intensifier video chain for processing said electrical signals from said radiation receiver to produce an image;

means for rotating said x-ray diagnostics system so that said x-ray source and said radiation receiver follow a circular path around an axis;

means for activating said x-ray source to emit x-rays during rotation of said x-ray diagnostics system so that said electrical signals are produced and processed during rotational movement of said x-ray diagnostics system to generate output signals from said x-ray image intensifier video chain; and means for integrating said output signals of said x-ray image intensifier video chain produced during rotational movement of said x-ray diagnostics system for generating a sharp image of a discrete region lying on said axis.

2. A medical apparatus as claimed in claim 1 wherein said means for operating said x-ray diagnostics system comprises means for controlling said means for rotating for causing said x-ray diagnostics system to execute a pendulum motion around a middle position.

3. A medical apparatus as claimed in claim 1 wherein said x-ray image intensifier video chain includes an analog-to-digital converter to which said electrical signals from said radiation receiver are supplied, and wherein said means for integrating comprises a digital memory contained in said x-ray image intensifier video chain and supplied with digital signals from said converter corresponding to said signals from said radiation receiver.

4. A medical apparatus comprising;

an x-ray diagnostics system having an x-ray source and a radiation receiver which produces electrical signals corresponding to x-rays incident thereon;

an x-ray image intensifier video chain for processing said electrical signals from said radiation receiver to produce an image;

means for rotating said x-ray diagnostics system so that said x-ray source and said radiation receiver follow a circular path around an axis;

means for activating said x-ray source to emit x-rays during rotation of said x-ray diagnostics system;

means for integrating said electrical signals from said radiation receiver produced during rotation of said x-ray diagnostics system for generating a sharp image of a discrete region lying on said axis; and means for treating a subject, located on said axis, with therapeutic radiation; and means for operating said x-ray diagnostics system for locating a therapeutically relevant region for treatment with said therapeutic radiation.

5. A medical apparatus as claimed in claim 4 wherein said means for operating said x-ray diagnostics system comprises means for transirradiating a subject with x-rays from said x-ray source from different transirradiation directions, said radiation receiver emitting signals corresponding to radiation incident thereon at each of said transirradiation directions, and wherein said means for operating said x-ray diagnostics system comprises means for operating said means for rotating said x-ray diagnostics system, said means for activating said x-ray source, and said means for integrating for causing said x-ray diagnostics system to be rotated and said x-ray source to be activated and said signals to be integrated for at least one of said transirradiation directions.

6. A medical apparatus as claimed in claim 5 wherein said means for operating said x-ray diagnostics system comprises means for controlling said means for rotating for causing said x-ray diagnostics system to execute a pendulum motion around a middle position.

7. A medical apparatus as claimed in claim 6 wherein said means for operating said x-ray diagnostics system comprises means for controlling said means for rotating for causing said x-ray diagnostics system to execute a pendulum motion around one of said transirradiation positions as said middle position.

8. A medical apparatus as claimed in claim 7 wherein said radiation source comprises an x-ray-transparent region through which x-rays emitted by said x-ray source pass in the transirradiation direction corresponding to the transirradiation position forming said middle position.

9. A medical apparatus as claimed in claim 5 wherein said means for producing an image includes means for integrating and storing a first image with a first integration time with said x-ray diagnostics system in a stationary position corresponding to one of said transirradiation positions, and means for producing a second image with a second integration time, which is shorter than said first integration time, with said x-ray diagnostics installation also in said stationary position corresponding to said one of said transirradiation positions.

10. A medical apparatus as claimed in claim 5 wherein said means for treating a subject with therapeutic radiation comprises means for emitting said therapeutic radiation in a series of therapeutic radiation pulses, wherein said means for generating an image comprises an x-ray image intensifier video chain including a video camera and means for supplying vertical pulses to said video camera for the operation thereof, and said medical apparatus including means connected to said means for emitting therapeutic radiation pulses, said means for activating said x-ray source and said means for generating said vertical pulses for synchronizing said therapeutic radiation pulses, the activation of said x-ray source, and the generation of said vertical pulses for causing the generation of an image in said the x-ray image intensifier video chain, the emission of x-rays, and the emission of a therapeutic radiation pulse to ensue substantially simultaneously.

11. A medical apparatus as claimed in claim 4 wherein said means for operating said the x-ray diagnostics system comprises means for operating said means for rotating for rotating said x-ray source and said radiation receiver around said axis into each of said transirradiation directions, and for operating said means for activating said x-ray source and said means for integrating for activating said x-ray source and integrating said electrical signals briefly before said x-ray diagnostics installation reaches a transirradiation position.

12. A medical apparatus as claimed in claim 4 wherein said means for treating a subject comprises means for emitting focused acoustic waves.

13. A medical apparatus comprising:

therapeutic radiation emitter means for emitting radiation for effecting therapy of a subject;

x-ray locating means for generating an image of a subject to be treated with said therapeutic radiation, said x-ray locating means including an x-ray image intensifier video chain having a video camera operable by a series of vertical pulses; and means for controlling operation of said therapeutic radiation emitter means for causing said therapeutic radiation emitter means to emit a pulse of said therapeutic radiation synchronized with each of said vertical pulses of said video camera.

14. A medical apparatus as claimed in claim 13 wherein said therapeutic radiation/emitter means comprises means for emitting focused acoustic waves.

15. A medical apparatus as claimed in claim 14 wherein said x-ray locating means includes an x-ray source and an x-ray receiver and means for rotating said x-ray source and said x-ray receiver around an axis, and wherein said means for emitting focused acoustic waves comprises means for emitting focused acoustic waves converging at a focus zone which lies on said axis, at least during said therapy.

16. A medical apparatus as claimed in claim 14 wherein said means for emitting focused acoustic waves comprises a shockwave source which emits shockwaves having an intensity sufficient for disintegrating a calculus in vivo in said examination subject.

17. A medical apparatus comprising:

an x-ray diagnostics system having an x-ray source and a radiation reception disposed opposite said x-ray source, said radiation receiver generating signals corresponding to x-rays incident thereon;

an x-ray image intensifier video chain, supplied with said signals, which generates an image from said signals; and said x-ray image intensifier video chain including means for integrating said signals with a first integration time to obtain a first integrated image, memory means for storing said first integration image, means for integrating said signals with a second integration time, which is shorter than said first integration time, to obtain a second integrated image with said x-ray diagnostics system in substantially the same position as for said first integrated image, means for subtracting said second integrated image from said first integrated image to obtain a subtraction image, and means for displaying said subtraction image.

18. A medical apparatus comprising:

an x-ray diagnostics system having an x-ray source and a radiation receiver which produces electrical signals corresponding to x-rays incident thereon;

means for rotating said x-ray diagnostics system so that said x-ray source and said radiation receiver follow a circular path around an axis;

means for activating said x-ray source to emit x-rays during rotation of said x-ray diagnostics system;

means for integrating said electrical signals from said radiation receiver for generating a sharp image of a discreet region lying on said axis; and means for processing said electrical signals to produce an image including subtractor means for subtracting from a first image produced by integrating said electrical signals from said radiation receiver with said x-ray diagnostics system in an stationary position, a second image produced by integrating said electrical signals from said radiation receiver while said x-ray diagnostics system is rotating.

19. A medical apparatus comprising:
an x-ray diagnostics system having an x-ray source and a radiation receiver which produces electrical signals corresponding to x-rays incident thereon;
means for rotating said x-ray diagnostics system so that said x-ray source and said radiation receiver follow a circular path around an axis;
means for activating said x-ray source to emit x-rays during rotation of said x-ray diagnostics system; and
means for processing said electrical signals to produce an image including means for integrating and storing a first image with a first integration time with said x-ray diagnostics system in a stationary position, and means for producing a second image with a second integration time, which is shorter than said first integration time, with said x-ray diagnostics installation also in said stationary position.

20. A medical apparatus as claimed in claim 19 further comprising means for treating a subject, located on said axis, with therapeutic radiation, and further comprising means for operating said x-ray diagnostics system for locating a therapeutically relevant region for treatment with said therapeutic radiation.

21. A medical apparatus as claimed in claim 20 wherein said means for operating said x-ray diagnostics system comprises means for transirradiating a subject with x-rays from said x-ray source from different transirradiation directions, said radiation receiver emitting signals corresponding to radiation incident thereon at each of said transirradiation directions, and wherein said means for operating said x-ray diagnostics system comprises means for operating said means for rotating said x-ray diagnostics system, said means for activating said x-ray source, and said means for integrating for causing said x-ray diagnostics system to be rotated and said x-ray source to be activated and said signals to be integrated for at least one of said transirradiation directions.

22. A medical apparatus as claimed in claim 20 wherein said means for treating a subject comprises means for emitting focused acoustic waves.

* * * * *